(12) United States Patent
Chen et al.

(10) Patent No.: US 12,109,431 B1
(45) Date of Patent: Oct. 8, 2024

(54) DISPLAY APPARATUS DRIVING METHOD, DISPLAY APPARATUS, AND ELECTRONIC DEVICE

(71) Applicant: HKC Corporation Limited, Guangdong (CN)

(72) Inventors: Qinglin Chen, Guangdong (CN); Rongrong Li, Guangdong (CN)

(73) Assignee: HKC CORPORATION LIMITED, Guangdong (CN)

( * ) Notice: Subject to any disclaimer, the term of this patent is extended or adjusted under 35 U.S.C. 154(b) by 0 days.

(21) Appl. No.: 18/388,376

(22) Filed: Nov. 9, 2023

(30) Foreign Application Priority Data

Mar. 23, 2023 (CN) .......................... 202310287254.5

(51) Int. Cl.
*A61N 5/06* (2006.01)
*G02F 1/133* (2006.01)

(52) U.S. Cl.
CPC ....... *A61N 5/0625* (2013.01); *G02F 1/13312* (2021.01); *A61N 2005/0626* (2013.01); *A61N 2005/063* (2013.01); *A61N 2005/0632* (2013.01); *A61N 2005/0642* (2013.01); *A61N 2005/0659* (2013.01)

(58) Field of Classification Search
CPC .......... A61N 5/0625; A61N 2005/0626; A61N 2005/063; A61N 2005/0632; A61N 2005/0642; A61N 2005/0659; G02F 1/13312
See application file for complete search history.

(56) References Cited

U.S. PATENT DOCUMENTS

| | | |
|---|---|---|
| 2005/0147137 A1 | 7/2005 | Slatkine |
| 2009/0184260 A1 | 7/2009 | Huttenberger et al. |
| 2015/0039061 A1 | 2/2015 | Hong et al. |
| 2015/0297912 A1 | 10/2015 | Planard-Luong |
| 2016/0297085 A1 | 10/2016 | Uit de Bulten et al. |
| 2020/0092971 A1 | 3/2020 | Tsubota |
| 2020/0371386 A1 | 11/2020 | Liou et al. |

FOREIGN PATENT DOCUMENTS

| | | |
|---|---|---|
| CN | 102182966 A | 9/2011 |
| CN | 203784737 U | 8/2014 |
| CN | 114377293 A | 4/2022 |

(Continued)

OTHER PUBLICATIONS

Chinese First Office Action dated May 5, 2023 issued in CN 202310287254.5.

(Continued)

*Primary Examiner* — Joseph A Stoklosa
*Assistant Examiner* — Adam J Avigan
(74) *Attorney, Agent, or Firm* — Scully, Scott, Murphy & Presser, P.C.

(57) ABSTRACT

A display apparatus driving method includes: obtaining, based on a trigger signal, a distance value between the display apparatus and a user that is acquired by a distance detector, determining whether the distance value is within a preset range; and controlling a near-infrared light emitter of the display apparatus to emit near-infrared light, if the distance value is within the preset range, where the near-infrared light is used to heat the skin of the user.

12 Claims, 7 Drawing Sheets

(56) References Cited

FOREIGN PATENT DOCUMENTS

| | | | |
|---|---|---|---|
| CN | 115542612 | A | 12/2022 |
| JP | 2005337697 | * | 12/2005 |
| KR | 20210088492 | A | 7/2021 |
| WO | 2021153893 | A1 | 8/2021 |

OTHER PUBLICATIONS

Chinese Second Office Action dated May 12, 2023 issued in CN 202310287254.5.
Notice of Allowance dated May 26, 2023 issued in CN 202310287254.5.

* cited by examiner

Determine the target near-infrared light working zone facing the user, based on the distance values acquired by the distance detectors in the plurality of near-infrared light working zones Control the near-infrared light emitter in the target near-infrared light working zone to emit the near-infrared light

DISPLAY APPARATUS DRIVING METHOD, DISPLAY APPARATUS, AND ELECTRONIC DEVICE

CROSS-REFERENCE TO RELATED APPLICATION(S)

This application claims priority to Chinese Patent Application No. 202310287254.5, filed Mar. 23, 2023, the entire disclosure of which is hereby incorporated by reference.

TECHNICAL FIELD

The present disclosure relates to the field of display technologies, and specifically, to a display apparatus driving method, a display apparatus, and an electronic device.

BACKGROUND

With the development of photoelectric display technology and semiconductor fabrication technology, Thin-Film-Transistor Liquid-Crystal Displays (TFT-LCDs) have become increasingly mature and have been more and more widely used due to their advantages such as being lightweight and portable.

However, in the related art, a display apparatus is generally only capable of displaying images. How to improve the functionality of a display apparatus has become a technical problem to be solved.

SUMMARY

According to a first aspect, the present disclosure provides a method for driving a display apparatus. The display apparatus includes a face detector. The method includes: obtaining, based on a trigger signal, a distance value between the display apparatus and a user that is acquired by a distance detector when a user face is detected by the face detector; determining whether the distance value is within a preset range; and controlling a near-infrared light emitter of the display apparatus to emit near-infrared light, if the distance value is within the preset range, where the near-infrared light is used to heat the skin of the user. A display region of the display apparatus comprises at least two near-infrared light working zones used for irradiating the user face. When the user face moves in front of the display apparatus, the display apparatus is configured to: determine a target near-infrared light working zone facing the user face, based on distance values acquired by distance detectors in the plurality of near-infrared light working zones; obtain a distance value between the target near-infrared light working zone and the user that is acquired by the distance detector; and control a near-infrared light emitter in the target near-infrared light working zone to emit the near-infrared light and control a near-infrared light emitter in a near-infrared light working zone other than the target near-infrared light working zone to stop emitting the near-infrared light.

According to a second aspect, the present disclosure provides a display apparatus, including a backlight module and a display panel that are arranged in a stacked manner. The display apparatus is driven by the method according to the first aspect. The backlight module includes: a near-infrared light emitter configured to emit near-infrared light, the near-infrared light being capable of heating a skin of the user; a distance detector configured to detect a distance value between the display apparatus and the user; and a controller electrically connected to the distance detector and the near-infrared light emitter, where when the controller determines that the distance value is within a preset range, the controller controls the near-infrared light emitter to emit the near-infrared light. The display apparatus further comprises a face detector configured to detect whether the skin of the user is a user face. A display region of the display apparatus comprises a plurality of near-infrared light working zones, and a working status of the near-infrared light emitter in the plurality of near-infrared light working zones is switched depending on a position of the user.

According to a third aspect, the present disclosure provides an electronic device, the electronic device includes a power supply apparatus and the display apparatus according to the second aspect.

BRIEF DESCRIPTION OF THE DRAWINGS

To describe the technical solutions in the embodiments of the present disclosure more clearly, the accompanying drawings for use in the embodiments are briefly described. Apparently, the accompanying drawings in the following description show merely some embodiments of the present disclosure, and persons of ordinary skill in the art may obtain other drawings from these accompanying drawings without creative efforts.

DETAILED DESCRIPTION

Figure 1:
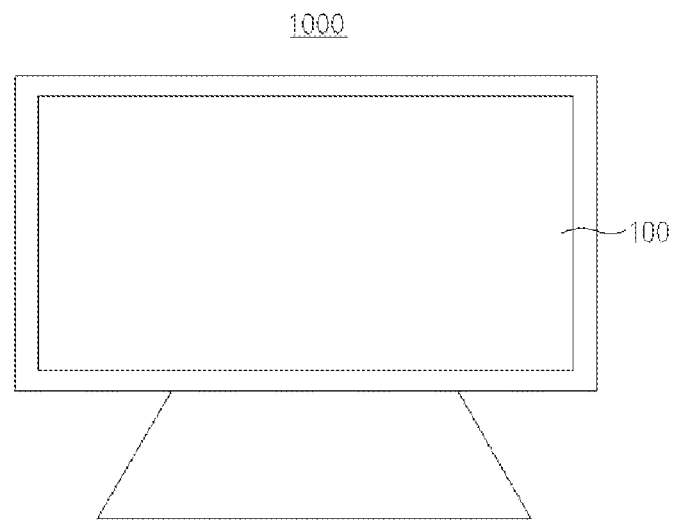
FIG. 1 is a schematic diagram of a structure of an electronic device according to an implementation of the present disclosure.

The technical solutions in the embodiments of the present disclosure will be described clearly and completely below with reference to the accompanying drawings in the embodiments of the present disclosure. Apparently, the described embodiments are only some rather than all of the embodiments of the present disclosure. All other embodiments obtained by persons of ordinary skill in the art based on the embodiments of the present disclosure without creative efforts shall fall within the scope of protection of the present disclosure.

The "embodiment" or "implementation" mentioned herein means that a particular feature, structure, or characteristic described with reference to the embodiment or implementation may be included in at least one embodiment of the present disclosure. This term appearing in various parts of the specification not necessarily refers to the same embodiment, nor an independent or alternative embodiment that is mutually exclusive to other embodiments. Persons skilled in the art understand explicitly or implicitly that the embodiment described herein may be combined with another embodiment.

It should be noted that the terms "first", "second", and the like in the specification, the claims, and the accompanying drawings of the present disclosure are used to distinguish different objects, rather than to describe a particular order. In addition, the terms "include" and "have" and any variations thereof are intended to cover a non-exclusive inclusion.

In the specification, for the sake of convenience, the illustration of a position relationship between constituent elements with reference to the accompanying drawings using the words such as "middle", "up", "down", "front", "rear", "left", "right", "vertical", "horizontal", "top", "bottom", "inner", and "outer" that indicate an orientation or position relationship is merely for ease and conciseness of description of the specification, rather than indicating or implying that the apparatuses or elements referred to must have a particular orientation or be constructed and operated in a particular orientation, and therefore shall not be construed as limiting the present disclosure. The position relationship between the constituent elements is appropriately changed depending on directions of the described constituent elements. Therefore, the position relationship is not limited to the words described in the specification, which may be appropriately replaced depending on the situation.

In the specification, the terms "mount", "join", and "connect" should be construed in a broad sense, unless otherwise expressly specified and defined. For example, a "connection" may be a fixed connection, a detachable connection, or an integral connection; or may be a mechanical connection or an electrical connection; or may be a direct connection, an indirect connection via an intermediary, or internal communication between two elements. Persons of ordinary skill in the art may understand the meanings of the above terms in the present disclosure based on the situation.

With the development of photoelectric display technology and semiconductor fabrication technology, Thin-Film-Transistor Liquid-Crystal Displays (TFT-LCDs) have become increasingly mature and have been more and more widely used due to their advantages such as being lightweight and portable.

However, in the related art, with the long-term development of liquid crystal display apparatus technologies, there is little difference between various types of display apparatus technologies, and a display apparatus can usually be used only for displaying images. Differentiated performance can make a product more competitive. Therefore, how to improve the functionality of a display apparatus becomes a technical problem to be solved.

Referring to FIG. 1, FIG. 1 is a schematic diagram of a structure of an electronic device according to an implementation of the present disclosure. The present disclosure provides a display apparatus 100 and an electronic device 1000 to solve the technical problem of how to improve the functionality of a display apparatus. The display apparatus 100 is applied in the electronic device 1000.

The electronic device 1000 may be, but is not limited to, a mobile phone, a tablet computer, a notebook computer, a palmtop computer, a Personal Computer (PC), a Personal Digital Assistant (PDA), a Portable Media Player (PMP), a self-driving car, a robotic vacuum cleaner, earphones, a camera, or another device.

The electronic device 1000 includes a power supply apparatus and the display apparatus 100. The power supply apparatus is configured to supply power to the display apparatus for operation.

Figure 2:
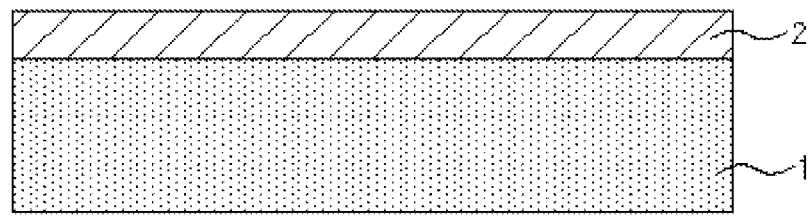
FIG. 2 is a schematic diagram of an overall structure of a display apparatus according to an implementation of the present disclosure.
Figure 3A:
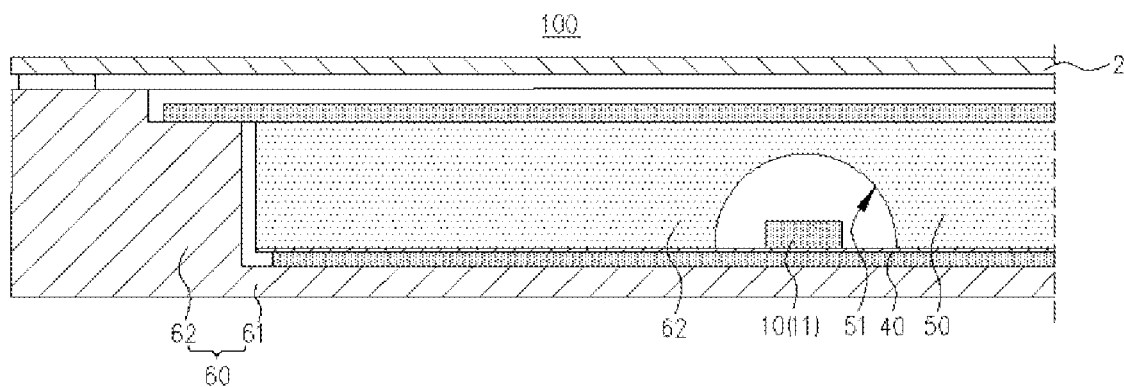
FIG. 3A is a schematic diagram of a sectional structure of the display apparatus according to an implementation of the present disclosure.
Figure 3B:
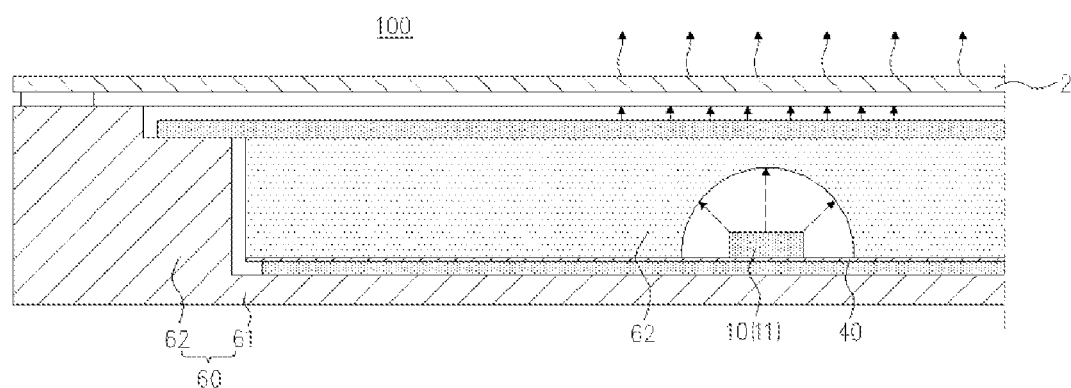
FIG. 3B is a schematic diagram of a light path of near-infrared light in the display apparatus according to an implementation of the present disclosure.
Figure 4:
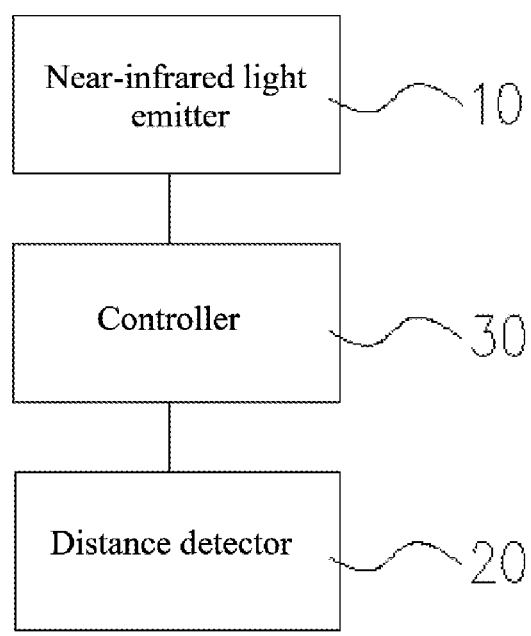
FIG. 4 is a schematic diagram of connection between a near-infrared light emitter, a distance detector, and a controller according to an implementation of the present disclosure.

Referring to FIG. 2, FIG. 3A, FIG. 3B, and FIG. 4, FIG. 2 is a schematic diagram of an overall structure of a display apparatus according to an implementation of the present disclosure, FIG. 3A is a schematic diagram of a sectional structure of the display apparatus according to an implementation of the present disclosure, FIG. 3B is a schematic diagram of a light path of near-infrared light in the display apparatus according to an implementation of the present disclosure, and FIG. 4 is a schematic diagram of connection between a near-infrared light emitter, a distance detector, and a controller according to an implementation of the present disclosure.

The display apparatus 100 includes a backlight module 1 and a display panel 2 that are arranged in a stacked manner. The backlight module 1 is configured to provide light rays to the display panel 2. The display panel 2 is configured to transmit the light rays from the backlight module 1 and form a displayed image, to display image information desired by the user.

The backlight module 1 includes a near-infrared light emitter 10, a distance detector 20, and a controller 30. The near-infrared light emitter 10 is configured to emit near-infrared light, and the near-infrared light is capable of heating the skin of the user. The distance detector 20 is configured to detect a distance value between the display apparatus 100 and the user. The controller 30 is electrically connected to the distance detector 20 and the near-infrared light emitter 10. When the controller 30 determines that the distance value is within a preset range, the controller 30 controls the near-infrared light emitter 10 to emit the near-infrared light.

The near-infrared light emitter 10 is configured to emit the near-infrared light, and the near-infrared light is capable of heating the skin of the user. The thermal action of the near-infrared light can not only promote the proliferation of collagen under the human skin, but also can increase blood circulation and promote the function of decomposing melanin.

The near-infrared light is an electromagnetic wave with a particular wavelength. Optionally, the wavelength of the near-infrared light in the present disclosure ranges from 900 nm to 1,800 nm. For example, the wavelength of the near-infrared light may be 900 nm, 950 nm, 1,000 nm, 1,200 nm, 1,500 nm, 1,530 nm, 1,780 nm, 1,800 nm, or another value within the range of 900 nm to 1,800 nm, which is not limited in the present disclosure. If the wavelength of the near-infrared light is less than 900 nm, the heating effect of the near-infrared light on the human skin may be significantly reduced. Because the near-infrared light is emitted by the near-infrared light emitter 10, the wavelength of the near-infrared light emitted by the near-infrared light emitter 10 is generally less than 1,800 nm due to a limited power of the near-infrared light emitter 10.

Specifically, electromagnetic waves in the band of 900 nm to 1,800 nm can penetrate the human epidermis, directly heat water molecules under the epidermis, empower damaged cells of the human body through thermal action, promote the repair and regeneration of deep collagen, accelerate blood circulation, and discharge pigmentation and skin metabolic waste. In addition, a safe temperature that the surface layer of the human skin can withstand ranges from 40° C. to 43° C. If the safe temperature is exceeded, there may be a risk of burns. The near-infrared light can quickly heat the skin of the user to 43° C. within 20 seconds, and can maintain the constant temperature in a large area, thereby improving the skin of the user condition.

The backlight module 1 further includes the distance detector 20. The distance detector 20 may be configured to detect the distance value between the user and the display apparatus 100. Optionally, the distance detector 20 includes, but is not limited to, a somatosensory sensor, an ultrasonic distance detector, a laser distance detector, or another type of distance detector.

The backlight module 1 further includes the controller 30. The controller 30 is electrically connected to the distance detector 20 and the near-infrared light emitter 10. The controller 30 may be configured to control the near-infrared light emitter 10 to work or not to work. Moreover, the controller 30 may control a working status of the near-infrared light emitter 10 based on the distance value between the user and the display apparatus 100. Specifically, the controller 30 controls the near-infrared light emitter 10 to work or not to work, by determining whether the distance value is within the preset range. For example, when the controller 30 determines that the distance value is within the preset range, the user is in an effective irradiation range of the near-infrared light emitter 10, and the controller 30 controls the near-infrared light emitter 10 to emit the near-infrared light. When the controller 30 determines that the distance value is outside the preset range, the near-infrared light emitted by the near-infrared light emitter 10 cannot act on the user, and the controller 30 controls the near-infrared light emitter 10 to stop emitting the near-infrared light.

Further, when the distance value is within the preset range (in other words, the user is within an effective skin care region of the display apparatus 100), the ranging sensor emits and transmits a first signal to the controller 30, and the controller 30 is configured to control, based on the first signal, the near-infrared light emitter 10 to emit the near-infrared light. When the distance value is outside the preset range (in other words, the user is not within the effective skin care region of the display apparatus 100), the ranging sensor emits and transmits a second signal to the controller 30, and the controller 30 is configured to control, based on the second signal, the near-infrared light emitter 10 to stop emitting the near-infrared light.

Optionally, positions of the distance detector 20 and the controller 30 are not limited in the present disclosure, and the distance detector 20 and the controller 30 may be arranged in the backlight module 1 or the display panel 2 or another apparatus.

In the display apparatus 100 provided by the present disclosure, the backlight module 1 includes the near-infrared light emitter 10, the distance detector 20, and the controller 30. The distance detector 20 is configured to detect the distance value between the display apparatus 100 and the user. When the controller 30 determines that the distance value is within the preset range, the controller 30 controls the near-infrared light emitter 10 to emit the near-infrared light, where the near-infrared light is capable of heating the skin of the user. At present, people's awareness of skin health is increasing, but the majority of people spend a long time in office and do not have enough time to maintain skin care. The near-infrared light emitted by the near-infrared light emitter 10 in the display apparatus 100 of the present disclosure can heat the skin of the user to promote the proliferation of deep collagen under the skin of the user, increase blood circulation, and promote the decomposition of melanin. The display apparatus 100 has excellent skin care functions, so that the user can complete skin care while working. Moreover, the display apparatus 100 of the present disclosure is not only simple to operate, but also low in cost, which is beneficial to mass production of the display apparatus 100.

Moreover, when the distance value between the user and the display apparatus 100 is within the preset range, the near-infrared light emitter 10 works and emits light, so that the near-infrared light emitted by the near-infrared light emitter 10 can act on the skin of the user to the greatest extent, which improves the working efficiency of the near-infrared light emitter 10, and can effectively reduce the energy loss of the display apparatus 100, improving the intelligence of the display apparatus 100.

Referring back to FIG. 2 and FIG. 3A, the backlight module 1 further includes a bearer 40, a light guide 50, and a back plate 60 that are arranged in sequence.

The back plate 60 includes a bottom plate 61 and a plurality of side plates 62 that surround the bottom plate 61 in sequence. The bottom plate 61 and the plurality of side plates 62 form an enclosed accommodation space.

The bearer 40 is disposed on the bottom plate of the back plate 60. The bearer 40 is configured to bear the near-infrared light emitter 10. Optionally, the bearer 40 includes, but is not limited to, a light panel.

The near-infrared light emitter 10 is disposed on the bearer 40.

The light guide 50 is disposed on the bottom plate 61. The light guide 50 is disposed on a side of the bearer 40 away from the bottom plate 61. The display panel 2 is disposed on a side of the light guide 50 away from the bearer 40. The light guide 50 is configured to homogenize the near-infrared light emitted by the near-infrared light emitter 10, and direct the near-infrared light toward the display panel 2. Optionally, the light guide 50 includes, but is not limited to, a light guide plate.

The light guide 50 is configured to increase an emission range of the near-infrared light in the display apparatus 100, thereby increasing the effective skin care region of the display apparatus 100.

In this implementation, the near-infrared light emitter 10 in the display apparatus 100 is mounted according to the following sequence: First, the back plate 60 is placed flat on an operating platform, and an adhesive strip for bonding the bearer 40 is attached; the bearer 40 and the near-infrared light emitter 10 are mounted on the adhesive strip; the light guide 50 is mounted on the side of the bearer 40 away from the bottom plate 61; and finally, an optical film and the display panel 2 are mounted.

Figure 5:
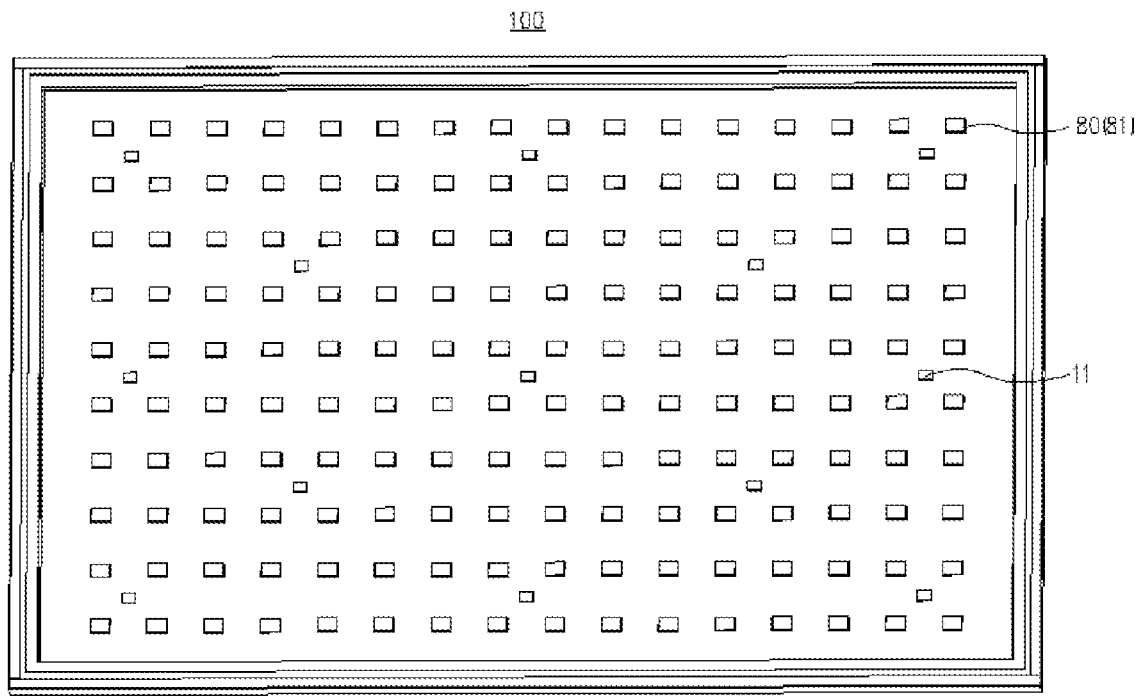
FIG. 5 is a schematic diagram of arrangement of the near-infrared light emitter and a visible light emitter in the display apparatus according to an implementation of the present disclosure.

Referring to FIG. 5, FIG. 5 is a schematic diagram of arrangement of the near-infrared light emitter and a visible light emitter in the display apparatus according to an implementation of the present disclosure.

In this implementation, a plurality of near-infrared light-emitting elements 11 in two adjacent columns are arranged in a staggered manner, so as to increase a range in which the plurality of near-infrared light-emitting elements 11 radiate the near-infrared light to the display panel 2, and improve the skin care effect of the display apparatus 100.

The backlight module 1 further includes a visible light emitter 80. The visible light emitter 80 includes a plurality of visible light-emitting elements 81 configured to emit visible light to the display panel 2 to form a displayed image.

Referring back to FIG. 3A, the near-infrared light emitter 10 includes a plurality of near-infrared light-emitting elements 11 configured to emit the near-infrared light, a side of the light guide 50 facing the bearer 40 is provided with a plurality of light guide notches 51, the near-infrared light-emitting element 11 is arranged in the light guide notch 51, and the near-infrared light emitted by the near-infrared light-emitting element 11 enters the light guide 50 through the light guide notch 51.

In this implementation, the near-infrared light-emitting element 11 is a near-infrared lamp bead. Both ends of the light guide notch 51 abut against the bearer 40. The light guide notch 51 accommodates the near-infrared light-emitting element 11, and prevents the near-infrared light emitted by the near-infrared light-emitting element 11 from being radiated to other parts, so as to improve a light utilization rate of the near-infrared light.

Optionally, in this implementation, the light guide notch 51 is a hemispherical notch.

The light guide notch 51 is a hemispherical notch, which can refract the near-infrared light incident on the light guide notch 51 to the light guide plate, and diverge the near-infrared light, increasing an incident range of the near-infrared light entering the light guide 50, so that the display apparatus 100 can refract the limited near-infrared light to the display panel 2 more comprehensively, achieving the best skin care effect. In addition, the provision of the light guide notch 51 can also reduce a number of the near-infrared light-emitting elements and reduce the cost.

Moreover, the light guide notch 51 may be configured to refract the near-infrared light, and refract a direction of the near-infrared light to be perpendicular to the display panel 2, improving the coverage effect of the near-infrared light in the display apparatus 100.

Figure 6:
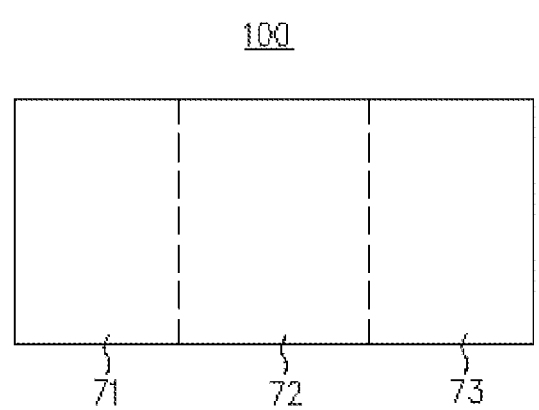
FIG. 6 is a schematic diagram of a display apparatus including a plurality of near-infrared light working zones according to another implementation of the present disclosure.

Referring to FIG. 2 and FIG. 6, FIG. 6 is a schematic diagram of a display apparatus including a plurality of near-infrared light working zones according to another implementation of the present disclosure. A display region of the display apparatus 100 includes a plurality of near-infrared light working zones, and at least one distance detector 20 and at least one near-infrared light-emitting element 11 are arranged in each of the near-infrared light working zones. When the user faces the display apparatus 100, the plurality of near-infrared light working zones include at least one target near-infrared light working zone, the distance value acquired by at least one distance detector 20 in the target near-infrared light working zone is within the preset range, and the controller 30 is configured to control the near-infrared light-emitting element 11 in the target near-infrared light working zone to work.

In other words, when the distance value acquired by the distance detector 20 is within the preset range, the near-infrared light working zone corresponding to the distance detector 20 is the target near-infrared light working zone, and the controller 30 controls the near-infrared light-emitting element 11 in the target near-infrared light working zone to work.

When the display apparatus 100 is a large-screen display, the display apparatus 100 includes a plurality of near-infrared light working zones. For example, in this implementation, the display apparatus 100 includes a first working zone 71, a second working zone 72, and a third working zone 73. When the user is facing the first working zone 71, the distance detector 20 in the first working zone 71 detects that a distance value between the user and the first working zone 71 is within the preset range, the controller 30 controls the near-infrared light-emitting element 11 in the first working zone 71 to emit the near-infrared light. Moreover, at this time, the near-infrared light-emitting elements 11 in the second working zone 72 and the third working zone 73 do not emit light. Similarly, it may also be possible that the near-infrared light-emitting element 11 in the second working zone 72 or the near-infrared light-emitting element 11 in the third working zone 73 works and emits light, or that the near-infrared light-emitting elements 11 in any two of the first working zone 71, the second working zone 72, and the third working zone 73 work and emit light, or that the near-infrared light-emitting elements 11 in the first working zone 71, the second working zone 72, and the third working zone 73 all work and emit light.

Moreover, if the user moves in front of the display apparatus 100, a working status of the near-infrared light-emitting elements 11 in the first working zone 71, the second working zone 72, and the third working zone 73 may be switched depending on a position of the user. Specifically, for example, when the user moves to the front of the first working zone 71, the near-infrared light-emitting element 11 in the first working zone 71 emits the near-infrared light; and when the user moves to the front of the second working zone 72, the near-infrared light-emitting element 11 in the second working zone 72 emits the near-infrared light, and the near-infrared light-emitting element 11 in the first working zone 71 stops working. The light emitting status of the plurality of near-infrared light-emitting elements 11 in the display apparatus 100 is switched depending on the user, which further improves the functionality of the display apparatus 100.

It should be noted that, in this implementation, the display apparatus 100 is divided into three near-infrared light working zones. Optionally, in other implementations, a number of the near-infrared light working zones may alternatively be two, four, five, six, or another number, which is not limited in the present disclosure.

The display apparatus 100 includes the plurality of near-infrared light working zones, and when the user is facing the near-infrared light working zone and is within an effective distance, the near-infrared light-emitting element 11 in the near-infrared light working zone of this region works and emits light. This enables the near-infrared light emitter 10 in the display apparatus 100 to work in different zones, which reduces the energy consumption of the display apparatus 100, and improves a utilization rate of the near-infrared light emitted by the display apparatus 100.

Figure 7:
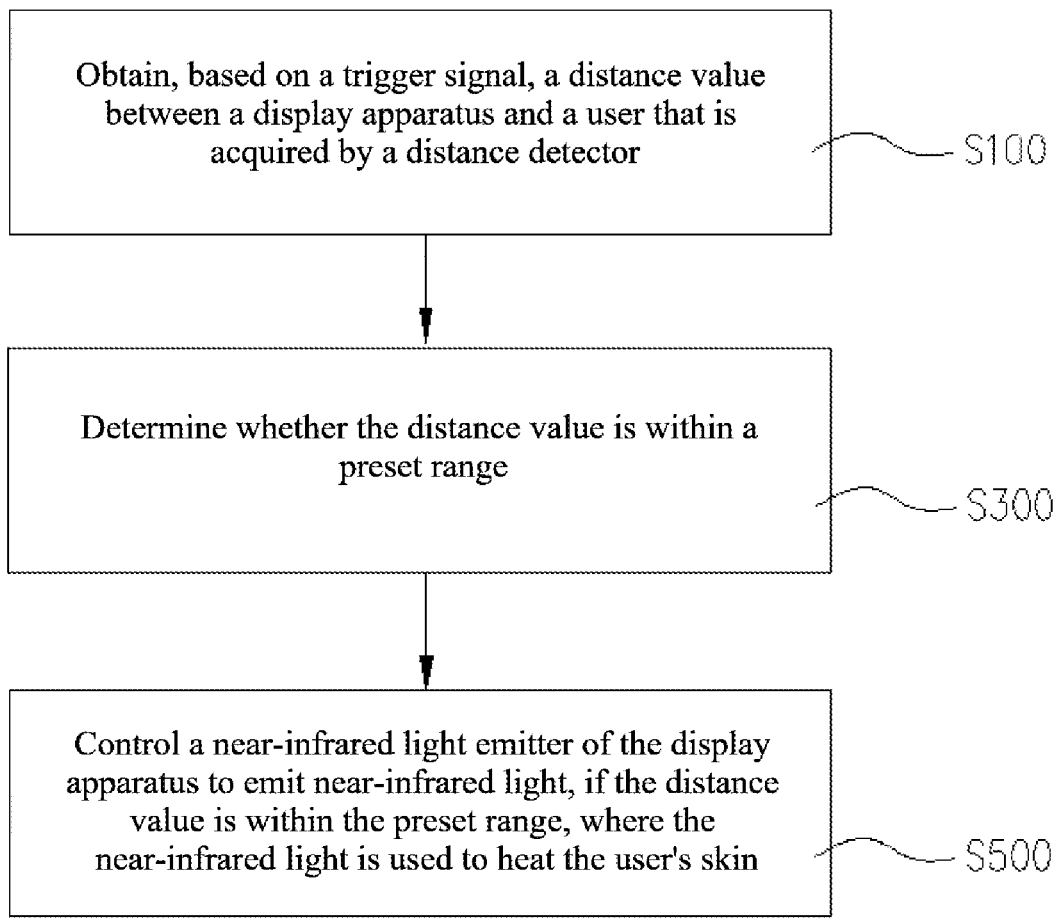
FIG. 7 is a flowchart of a display apparatus driving method according to an implementation of the present disclosure.

Referring to FIG. 7, FIG. 7 is a flowchart of a display apparatus driving method according to an implementation of the present disclosure. The present disclosure further provides a display apparatus driving method, which is applied to the display apparatus 100. The display apparatus driving method includes, but is not limited to, steps S100, S300, and S500, and the detailed description of steps S100, S300, and S500 is as follows.

S100: A distance value between the display apparatus 100 and a user that is acquired by a distance detector 20 is obtained based on a trigger signal.

The trigger signal is an enable signal of an infrared skin care function in the display apparatus 100. In other words, when the display apparatus 100 receives the trigger signal, the controller 30 controls the near-infrared light emitter 10 in the display apparatus 100 to emit light or not to emit light.

The distance detector 20 may be configured to acquire the distance value between the user and the display apparatus 100. Optionally, the distance detector 20 includes, but is not limited to, a somatosensory sensor, an ultrasonic distance detector, a laser distance detector, or another type of detector.

S300: It is determined whether the distance value is within a preset range.

It is determined whether the distance value is within the preset range, and it may be determined whether the user is within an effective skin care region of the display apparatus 100, depending on whether the distance value is within the preset range. If the distance value is within the preset range, the user is within the effective skin care region of the display apparatus 100. If the distance value is not within the preset range, the user is not within the effective skin care region of the display apparatus 100.

The preset range is not limited in the present disclosure, and may be adjusted according to a power of the near-infrared light emitter 10. In this implementation, the preset range is 0 cm to 100 cm. In other implementations, the preset range may alternatively be 0 cm to 70 cm, 0 cm to 80 cm, 20 cm to 90 cm, or another value range, which is not limited in the present disclosure.

S500: A near-infrared light emitter 10 of the display apparatus 100 is controlled to emit near-infrared light, if the distance value is within the preset range, where the near-infrared light is used to heat the skin of the user.

When the distance value is within the preset range, the user is within the effective skin care region of the display apparatus 100, the controller 30 controls the near-infrared light emitter 10 of the display apparatus 100 to emit near-infrared light. The near-infrared light is used to heat the skin of the user, and empower damaged cells of the human body through thermal action, promote the repair and regeneration of deep collagen, accelerate blood circulation, and discharge pigmentation and skin metabolic waste.

In the display apparatus driving method provided by the present disclosure, the distance value between the display apparatus 100 and the user is obtained based on the trigger signal; it is determined whether the distance value is within the preset range; and the near-infrared light emitter 10 of the display apparatus 100 is controlled to emit near-infrared light, if the distance value is within the preset range, where the near-infrared light is used to heat the skin of the user. In the display apparatus driving method provided by the present disclosure, when the distance value between the user and the display apparatus 100 is within the preset range, the near-infrared light emitter 10 works and emits light, so that the near-infrared light emitted by the near-infrared light emitter 10 can act on the skin of the user to the greatest extent, which can effectively reduce the energy loss of the display apparatus 100.

Moreover, the near-infrared light emitted by the near-infrared light emitter 10 can heat the skin of the user to promote the proliferation of deep collagen under the skin of the user, increase blood circulation, and promote the decomposition of melanin. The display apparatus 100 has excellent skin care functions, so that the user can complete skin care while working. Moreover, the display apparatus 100 of the present disclosure is not only simple to operate, but also low in cost, which is beneficial to mass production of the display apparatus 100.

In an implementation, the display apparatus 100 includes a face detector, and the face detector may be configured to detect whether the skin of the user is a human face. Optionally, the face detector includes, but is not limited to, a 3D structured light module, which further improves the intelligence of the display apparatus 100.

Figure 8:
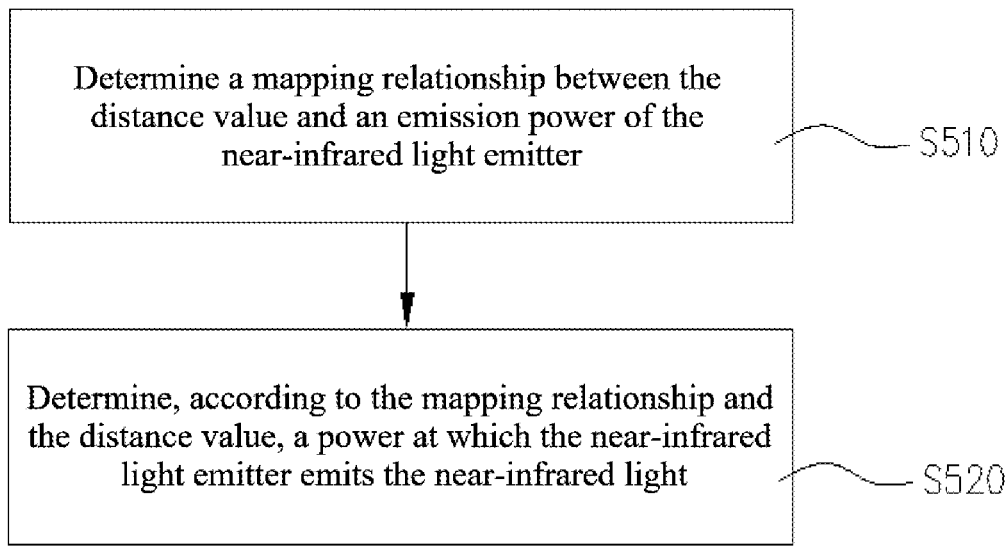
FIG. 8 is a flowchart 1 of steps further included by S500 in the display apparatus driving method according to an implementation of the present disclosure.

Referring to FIG. 8, FIG. 8 is a flowchart 1 of steps further included by S500 in the display apparatus driving method according to an implementation of the present disclosure. The "controlling a near-infrared light emitter 10 of the display apparatus 100 to emit near-infrared light, if the distance value is within the preset range" in S500 further includes S510 and S520, and the detailed description of steps S510 and S520 is as follows.

S510: A mapping relationship between the distance value and an emission power of the near-infrared light emitter 10 is determined.

When the distance value is relatively large, it indicates that the user is far away from the display apparatus 100. In order to ensure the skin care effect of the display apparatus 100 on the skin of the user, the near-infrared light emitted by the near-infrared light emitter 10 needs to radiate farther. In other words, the emission power of the near-infrared light emitter 10 needs to be higher. In conclusion, a larger distance value requires a higher emission power of the near-infrared light emitter 10; and a smaller distance value requires a lower emission power of the near-infrared light emitter 10. In other words, the distance value is positively correlated with the emission power of the near-infrared light emitter 10.

It should be noted that the mapping relationship between the distance value and the emission power of the near-infrared light emitter 10 is not specifically limited in the present disclosure.

S520: A power at which the near-infrared light emitter 10 emits the near-infrared light is determined according to the mapping relationship and the distance value.

The power at which the near-infrared light emitter 10 emits the near-infrared light is determined according to the mapping relationship and the distance value, and is input to the near-infrared light emitter 10 through the controller 30, so that the near-infrared light emitter 10 emits light. Thus, the skin care effect of the near-infrared light emitted by the near-infrared light emitter 10 on the skin of the user is ensured.

Figure 9:
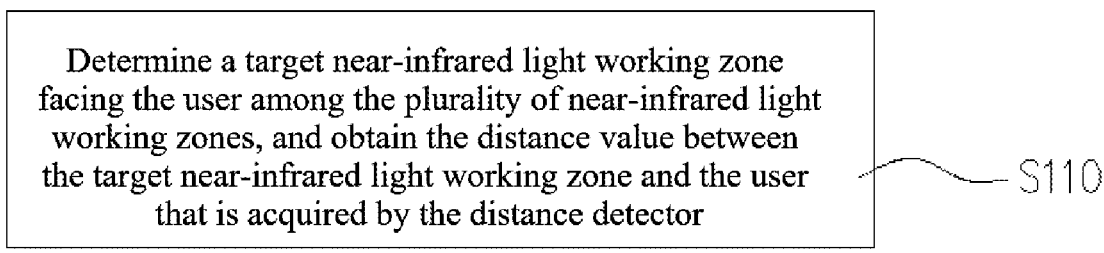
FIG. 9 is a flowchart of a step further included by S100 in the display apparatus driving method according to an implementation of the present disclosure.

Referring to FIG. 9, FIG. 9 is a flowchart of a step further included by S100 in the display apparatus driving method according to an implementation of the present disclosure. The "obtaining a distance value between the display apparatus 100 and a user that is acquired by a distance detector 20" in S100 further includes S110, and the detailed description of step S110 is as follows.

S110: A target near-infrared light working zone facing the user is determined among the plurality of near-infrared light working zones, and the distance value between the target near-infrared light working zone and the user that is acquired by the distance detector 20 is obtained.

The target near-infrared light working zone facing the user is determined among the plurality of near-infrared light working zones, and the near-infrared light emitter 10 of the target near-infrared light working zone works, which enables the near-infrared light emitter 10 in the display apparatus 100 to work in different zones, further reduces the energy consumption of the display apparatus 100, and improves a utilization rate of the near-infrared light emitted by the display apparatus 100.

Figure 10:
FIG. 10 is a flowchart of a step further included by S110 in the display apparatus driving method according to an implementation of the present disclosure.

Referring to FIG. 10, FIG. 10 is a flowchart of a step further included by S110 in the display apparatus driving method according to an implementation of the present disclosure. The "determining a target near-infrared light working zone facing the user among the plurality of near-infrared light working zones" in S110 includes S111, and the detailed description of step S111 is as follows.

S111: The target near-infrared light working zone facing the user is determined based on the distance values acquired by the distance detectors 20 in the plurality of near-infrared light working zones.

Specifically, the display apparatus 100 may include the plurality of near-infrared light working zones, and when the user is facing the near-infrared light working zone and is within the preset range, the near-infrared light working zone is the target near-infrared light working zone, and the near-infrared light-emitting element 11 in this region works and emits light.

Figure 11:
FIG. 11 is a flowchart 2 of a step further included by S500 in the display apparatus driving method according to an implementation of the present disclosure.

Referring to FIG. 11, FIG. 11 is a flowchart 2 of a step further included by S500 in the display apparatus driving method according to an implementation of the present disclosure. The "controlling a near-infrared light emitter 10 of the display apparatus 100 to emit near-infrared light" in S500 includes S501, and the detailed description of step S501 is as follows.

S501: The near-infrared light emitter in the target near-infrared light working zone is controlled to emit the near-infrared light.

The near-infrared light emitter 10 of the target near-infrared light working zone works, which enables the near-infrared light emitter 10 in the display apparatus 100 to work in different zones, further reduces the energy consumption of the display apparatus 100, and improves a utilization rate of the near-infrared light emitted by the display apparatus 100.

An objective of the present disclosure is to provide a display apparatus driving method, a display apparatus, and an electronic device, so as to solve the technical problem of how to improve the functionality of a display apparatus.

According to a first aspect, the present disclosure provides a display apparatus driving method. The display apparatus driving method includes: obtaining, based on a trigger signal, a distance value between the display apparatus and a user that is acquired by a distance detector; determining whether the distance value is within a preset range; and controlling a near-infrared light emitter of the display apparatus to emit near-infrared light, if the distance value is within the preset range, where the near-infrared light is used to heat the skin of the user.

In the display apparatus driving method provided by the present disclosure, the distance value between the display apparatus and the user is obtained based on the trigger signal; it is determined whether the distance value is within the preset range; and the near-infrared light emitter of the display apparatus is controlled to emit near-infrared light, if the distance value is within the preset range, where the near-infrared light is used to heat the skin of the user. In the display apparatus driving method provided by the present disclosure, when the distance value between the user and the display apparatus is within the preset range, the near-infrared light emitter works and emits light, so that the near-infrared light emitted by the near-infrared light emitter can act on the skin of the user to the greatest extent, which improves the working efficiency of the near-infrared light emitter, and can effectively reduce the energy loss of the display apparatus, improving the intelligence of the display apparatus.

Moreover, the near-infrared light emitted by the near-infrared light emitter can heat the skin of the user to promote the proliferation of deep collagen under the skin of the user, increase blood circulation, and promote the decomposition of melanin. The display apparatus has excellent skin care functions, so that the user can complete skin care while working.

The "controlling a near-infrared light emitter of the display apparatus to emit near-infrared light, if the distance value is within the preset range" includes: determining a mapping relationship between the distance value and an emission power of the near-infrared light emitter; and determining, according to the mapping relationship and the distance value, a power at which the near-infrared light emitter emits the near-infrared light.

A display region of the display apparatus includes a plurality of near-infrared light working zones, and the "obtaining a distance value between the display apparatus and a user that is acquired by a distance detector" includes: determining a target near-infrared light working zone facing the user among the plurality of near-infrared light working zones, and obtaining the distance value between the target near-infrared light working zone and the user that is acquired by the distance detector.

The "determining a target near-infrared light working zone facing the user among the plurality of near-infrared light working zones" includes: determining the target near-infrared light working zone facing the user, based on the distance values acquired by the distance detectors in the plurality of near-infrared light working zones; and the "controlling a near-infrared light emitter of the display apparatus to emit near-infrared light" includes: controlling the near-infrared light emitter in the target near-infrared light working zone to emit the near-infrared light.

According to a second aspect, the present disclosure provides a display apparatus, including a backlight module and a display panel that are arranged in a stacked manner. The backlight module includes: a near-infrared light emitter configured to emit near-infrared light, the near-infrared light being capable of heating a skin of the user; a distance detector configured to detect a distance value between the display apparatus and the user; and a controller electrically connected to the distance detector and the near-infrared light emitter, where when the controller determines that the distance value is within a preset range, the controller controls the near-infrared light emitter to emit the near-infrared light.

The backlight module further includes a bearer, a light guide, and a back plate that are arranged in sequence, the back plate includes a bottom plate and a plurality of side plates that surround the bottom plate in sequence, the near-infrared light emitter is arranged on the bearer, the light guide is arranged on the bottom plate, and the light guide is configured to homogenize the near-infrared light emitted by the near-infrared light emitter, and direct the near-infrared light toward the display panel.

The near-infrared light emitter includes a plurality of near-infrared light-emitting elements configured to emit the near-infrared light, a side of the light guide facing the bearer is provided with a plurality of light guide notches, the near-infrared light-emitting element is arranged in the light guide notch, and the near-infrared light emitted by the near-infrared light-emitting element enters the light guide through the light guide notch.

The light guide notch is a hemispherical notch.

A display region of the display apparatus includes a plurality of near-infrared light working zones, and at least one distance detector and at least one near-infrared light-emitting element are arranged in each of the near-infrared light working zones; and when the user faces the display apparatus, the plurality of near-infrared light working zones include at least one target near-infrared light working zone, the distance value acquired by at least one distance detector in the target near-infrared light working zone is within the preset range, and the controller is configured to control the near-infrared light-emitting element in the target near-infrared light working zone to work.

According to a third aspect, the present disclosure provides an electronic device, the electronic device includes a power supply apparatus and the display apparatus.

The above describes some implementations of the present disclosure, and it should be noted that for persons of ordinary skill in the art, several improvements and modifications can also be made without departing from the principle of the present disclosure, and these improvements and modifications are also considered to be within the scope of protection of the present disclosure.

What is claimed is:

1. A method for driving a display apparatus, the display apparatus comprising a face detector, the method comprising:
    obtaining, based on a trigger signal, a distance value between the display apparatus and a user that is acquired by a distance detector when a user face is detected by the face detector;
    determining whether the distance value is within a preset range; and
    controlling a near-infrared light emitter of the display apparatus to emit near-infrared light, if the distance value is within the preset range, wherein the near-infrared light is used to heat a skin of the user,
    wherein a display region of the display apparatus comprises at least two near-infrared light working zones used for irradiating the user face, and when the user face moves in front of the display apparatus, the display apparatus is configured to:
        determine a target near-infrared light working zone facing the user face, based on distance values acquired by distance detectors in the plurality of near-infrared light working zones;
        obtain a distance value between the target near-infrared light working zone and the user that is acquired by the distance detector; and
        control a near-infrared light emitter in the target near-infrared light working zone to emit the near-infrared light and control a near-infrared light emitter in a near-infrared light working zone other than the target near-infrared light working zone to stop emitting the near-infrared light.

2. The method for driving the display apparatus according to claim 1, wherein the controlling a near-infrared light emitter of the display apparatus to emit near-infrared light comprises:
    determining a mapping relationship between the distance value and an emission power of the near-infrared light emitter; and
    determining, according to the mapping relationship and the distance value, a power at which the near-infrared light emitter emits the near-infrared light.

3. A display apparatus driven by the method according to claim 1, wherein the display apparatus comprises a backlight module and a display panel that are arranged in a stacked manner, and the backlight module comprises:
    a near-infrared light emitter configured to emit near-infrared light, the near-infrared light being capable of heating a skin of the user;
    a distance detector configured to detect a distance value between the display apparatus and the user;
    a controller electrically connected to the distance detector and the near-infrared light emitter, wherein when the controller determines that the distance value is within a preset range, the controller controls the near-infrared light emitter to emit the near-infrared light; and
    a face detector configured to detect whether the skin of the user is a user face,
    wherein a display region of the display apparatus comprises a plurality of near-infrared light working zones, and a working status of the near-infrared light emitter in the plurality of near-infrared light working zones is switched depending on a position of the user.

4. The display apparatus according to claim 3, wherein the backlight module further comprises a bearer, a light guide, and a back plate that are arranged in sequence, the back plate comprises a bottom plate and a plurality of side plates that surround the bottom plate in sequence, the near-infrared light emitter is arranged on the bearer, the light guide is arranged on the bottom plate, and the light guide is configured to homogenize the near-infrared light emitted by the near-infrared light emitter, and direct the near-infrared light toward the display panel.

5. The display apparatus according to claim 4, wherein the near-infrared light emitter comprises a plurality of near-infrared light-emitting elements configured to emit the near-infrared light, a side of the light guide facing the bearer is provided with a plurality of light guide notches, the near-infrared light-emitting element is arranged in the light guide notch, and the near-infrared light emitted by the near-infrared light-emitting element enters the light guide through the light guide notch.

6. The display apparatus according to claim 5, wherein the light guide notch is a hemispherical notch.

7. The display apparatus according to claim 5, wherein at least one distance detector and at least one near-infrared light-emitting element are arranged in each of the near-infrared light working zones; and when the user faces the display apparatus, the plurality of near-infrared light working zones comprise at least one target near-infrared light working zone, the distance value acquired by at least one distance detector in the target near-infrared light working zone is within the preset range, and the controller is configured to control the near-infrared light-emitting element in the target near-infrared light working zone to work.

8. An electronic device, wherein the electronic device comprises a power supply apparatus and a display apparatus driven by the method according to claim 1, the display apparatus comprising a backlight module and a display panel that are arranged in a stacked manner, wherein the backlight module comprises:
    a near-infrared light emitter configured to emit near-infrared light, the near-infrared light being capable of heating a skin of the user;
    a distance detector configured to detect a distance value between the display apparatus and the user;
    a controller electrically connected to the distance detector and the near-infrared light emitter, wherein when the controller determines that the distance value is within a preset range, the controller controls the near-infrared light emitter to emit the near-infrared light; and
    a face detector configured to detect whether the skin of the user is a user face, wherein a display region of the display apparatus comprises a plurality of near-infrared light working zones, and a working status of the near-infrared light emitter in the plurality of near-infrared light working zones is switched depending on a position of the user.

9. The electronic device according to claim 8, wherein the backlight module further comprises a bearer, a light guide, and a back plate that are arranged in sequence, the back plate comprises a bottom plate and a plurality of side plates that surround the bottom plate in sequence, the near-infrared light emitter is arranged on the bearer, the light guide is arranged on the bottom plate, and the light guide is configured to homogenize the near-infrared light emitted by the near-infrared light emitter, and direct the near-infrared light toward the display panel.

10. The electronic device according to claim 9, wherein the near-infrared light emitter comprises a plurality of near-infrared light-emitting elements configured to emit the near-infrared light, a side of the light guide facing the bearer is provided with a plurality of light guide notches, the near-infrared light-emitting element is arranged in the light guide notch, and the near-infrared light emitted by the near-infrared light-emitting element enters the light guide through the light guide notch.

11. The electronic device according to claim 10, wherein the light guide notch is a hemispherical notch.

12. The electronic device according to claim 10, wherein a display region of the display apparatus comprises a plurality of near-infrared light working zones, and at least one distance detector and at least one near-infrared light-emitting element are arranged in each of the near-infrared light working zones; and when the user faces the display apparatus, the plurality of near-infrared light working zones comprise at least one target near-infrared light working zone, the distance value acquired by at least one distance detector in the target near-infrared light working zone is within the preset range, and the controller is configured to control the near-infrared light-emitting element in the target near-infrared light working zone to work.

* * * * *